(12) United States Patent
Horrisberger et al.

(10) Patent No.: US 12,082,775 B2
(45) Date of Patent: Sep. 10, 2024

(54) RADIALLY-DIRECTED BALLOON VISUALIZATION DEVICE

(71) Applicants: BOSTON SCIENTIFIC SCIMED, INC., Maple Grove, MN (US); MAYO FOUNDATION FOR MEDICAL EDUCATION AND RESEARCH, Rochester, MN (US)

(72) Inventors: Benn Horrisberger, Blaine, MN (US); James P. Rohl, Prescott, WI (US); Lance A. Freeseman, Greenfield, MN (US); James A. Klos, Bay City, WI (US); Joel T. Eggert, Plymouth, MN (US); Arjun D. Sharma, St. Paul, MN (US); Samuel J. Asirvatham, Rochester, MN (US)

(73) Assignees: BOSTON SCIENTIFIC SCIMED, INC., Maple Grove, MN (US); MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 1707 days.

(21) Appl. No.: 16/312,282

(22) PCT Filed: Dec. 16, 2016

(86) PCT No.: PCT/US2016/067253
§ 371 (c)(1),
(2) Date: Dec. 20, 2018

(87) PCT Pub. No.: WO2017/106698
PCT Pub. Date: Jun. 22, 2017

(65) Prior Publication Data
US 2019/0142246 A1    May 16, 2019

Related U.S. Application Data

(60) Provisional application No. 62/269,591, filed on Dec. 18, 2015.

(51) Int. Cl.
A61B 1/00 (2006.01)
A61B 1/05 (2006.01)
(Continued)

(52) U.S. Cl.
CPC ...... *A61B 1/00082* (2013.01); *A61B 1/00177* (2013.01); *A61B 1/051* (2013.01);
(Continued)

(58) Field of Classification Search
CPC ... A61B 1/00082; A61B 1/00177; A61B 1/05; A61B 1/051; A61B 1/3137;
(Continued)

(56) References Cited

U.S. PATENT DOCUMENTS 4,961,738 A    10/1990 Mackin
5,588,951 A    12/1996 Zhu et al.
(Continued)

FOREIGN PATENT DOCUMENTS

EP    1870018 A2    12/2007
JP    H06507809 A    9/1994
(Continued)

OTHER PUBLICATIONS

International Search Report and Written Opinion dated May 2, 2017 for International Application No. PCT/US2016/067253.
(Continued)

*Primary Examiner* — Boniface N Nganga
(74) *Attorney, Agent, or Firm* — Seager, Tufte & Wickhem, LLP

(57) ABSTRACT

A visualization catheter includes an elongate shaft, a cap portion, and an offset balloon coupled to the distal end of the shaft. The elongate shaft includes a proximal end, a distal end, and a central axis defined therebetween. The cap portion is coupled to the distal end of the shaft. The cap portion also includes a visualization element and defines an
(Continued)

aperture. The offset balloon is coupled to the distal end of the shaft and encapsulates the cap portion. The offset balloon defines a center point offset relative to the central axis of the shaft.

12 Claims, 6 Drawing Sheets

(51) Int. Cl.
| | | |
|---|---|---|
| *A61B 1/313* | (2006.01) | |
| *A61B 8/00* | (2006.01) | |
| *A61B 8/08* | (2006.01) | |
| *A61B 90/00* | (2016.01) | |
| *A61L 29/02* | (2006.01) | |
| *A61L 29/06* | (2006.01) | |
| *A61L 29/14* | (2006.01) | |
| *A61M 25/10* | (2013.01) | |

(52) U.S. Cl.
CPC .......... *A61B 1/3137* (2013.01); *A61B 8/0883* (2013.01); *A61B 8/445* (2013.01); *A61B 90/36* (2016.02); *A61B 90/37* (2016.02); *A61L 29/02* (2013.01); *A61L 29/06* (2013.01); *A61L 29/14* (2013.01); *A61B 1/05* (2013.01); *A61B 2090/373* (2016.02); *A61B 2090/3784* (2016.02); *A61M 25/1002* (2013.01); *A61M 25/1011* (2013.01); *A61M 2025/1013* (2013.01); *A61M 2025/1086* (2013.01)

(58) Field of Classification Search
CPC ...... A61B 2090/373; A61B 2090/3784; A61B 8/0883; A61B 8/445; A61B 90/36; A61B 90/37; A61L 29/06; A61L 29/14; A61M 2025/1013; A61M 2025/1086; A61M 25/1002; A61M 25/1011
See application file for complete search history.

(56) References Cited

U.S. PATENT DOCUMENTS

| | | | |
|---|---|---|---|
| 7,666,203 B2 | 2/2010 | Chanduszko et al. | |
| 8,172,747 B2 | 5/2012 | Wallace et al. | |
| 8,900,214 B2 | 12/2014 | Nance et al. | |
| 2002/0150707 A1* | 10/2002 | Wilkins | A61L 29/049 |
| | | | 428/35.2 |
| 2005/0080313 A1 | 4/2005 | Stewart et al. | |
| 2005/0228452 A1* | 10/2005 | Mourlas | A61M 25/1002 |
| | | | 606/41 |
| 2005/0245882 A1 | 11/2005 | Elkins et al. | |
| 2007/0293724 A1 | 12/2007 | Saadat et al. | |
| 2009/0082634 A1 | 3/2009 | Kathrani et al. | |
| 2009/0318759 A1 | 12/2009 | Jacobsen et al. | |
| 2010/0010311 A1 | 1/2010 | Miller et al. | |
| 2010/0094209 A1 | 4/2010 | Drasler et al. | |
| 2012/0065469 A1* | 3/2012 | Allyn | A61B 5/0013 |
| | | | 600/109 |
| 2013/0245371 A1 | 9/2013 | Mourlas et al. | |
| 2014/0221749 A1* | 8/2014 | Grant | A61B 1/015 |
| | | | 600/109 |
| 2014/0357956 A1* | 12/2014 | Salahieh | A61N 1/37247 |
| | | | 348/77 |
| 2015/0314110 A1 | 11/2015 | Park | |
| 2015/0327754 A1* | 11/2015 | Leeflang | A61B 1/128 |
| | | | 600/109 |
| 2017/0135559 A1 | 5/2017 | Horrisberger et al. | |
| 2017/0296795 A1 | 10/2017 | Troutman et al. | |

FOREIGN PATENT DOCUMENTS

| | | |
|---|---|---|
| JP | H1051589 A | 2/1998 |
| JP | 2001518808 A | 10/2001 |
| JP | 2007535970 A | 12/2007 |
| JP | 2009543607 A | 12/2009 |
| JP | 2011525132 A | 9/2011 |
| JP | 2012505050 A | 3/2012 |
| JP | 2013508118 A | 3/2013 |
| JP | 2015163088 A | 9/2015 |
| WO | 9221292 A2 | 12/1992 |
| WO | 9640347 A1 | 12/1996 |
| WO | 2005037363 A2 | 4/2005 |
| WO | 2008008796 A2 | 1/2008 |
| WO | 2014165130 A2 | 10/2014 |
| WO | 2015057533 A1 | 4/2015 |

OTHER PUBLICATIONS

International Preliminary Report on Patentability dated Jun. 28, 2018 for International Application No. PCT/US2016/067253.
Invitation to Pay Additional Fees dated Jul. 26, 2017 for International Application No. PCT/US2017/028140.
International Search Report and Written Opinion dated Sep. 19, 2017 for International Application No. PCT/US2017/028140.
International Preliminary Report on Patentability dated May 24, 2018 for International Application No. PCT/US2016/061714.
International Search Report and Written Opinion dated Jan. 24, 2017 for International Application No. PCT/US2016/061714.

* cited by examiner

RADIALLY-DIRECTED BALLOON VISUALIZATION DEVICE

CROSS-REFERENCE TO RELATED APPLICATIONS

This application is a National Stage of International Application No. PCT/US2016/067253, filed Dec. 16, 2016, which claims the benefit of priority under 35 U.S.C. § 119 to U.S. Provisional Application Ser. No. 62/269,591 filed Dec. 18, 2015, the entire disclosures of which are incorporated herein by reference.

TECHNICAL FIELD

The present invention relates to radially-directed balloon visualization devices and methods related thereto.

BACKGROUND

Heart function can be significantly impaired when a heart valve is not performing properly. Potential causes for heart valve malfunction include dilation of an annulus around the valve, ventricular dilation, and a prolapsed or misshapen valve leaflet. When the heart valve is unable to close properly, blood within a heart chamber can leak backwards through the valve, which is commonly referred to as regurgitation.

Valve regurgitation may be treated by replacing or repairing a diseased valve. Although open heart surgery is one method for treating the diseased valve, a less invasive methods of treatment would be more desirable for many patients. Minimally invasive procedures, however, are significantly limited by the lack of adequate visualization through blood within a patient's beating heart. Accordingly, there is a need for alternative devices, systems and methods for treating heart valve disease that provide adequate visualization for users during a minimally invasive procedure.

SUMMARY

This document relates to various embodiments of radially-directed balloon visualization devices and methods related thereto. Balloon-based visualization devices and methods provided herein include features that can improve minimally invasive surgical techniques used during a heart valve repair procedure for repairing a heart valve, e.g., a tricuspid or mitral valve. While devices, systems and methods provided herein may be described with respect to a tricuspid valve repair, other types of minimally invasive surgical procedures can also be contemplated. For example, the devices and methods provided herein may, in some cases, be advantageously applied to tissue repair procedures in the other areas of the heart, or other locations within the body, such as the peripheral vasculature.

In Example 1, a visualization catheter includes an elongate shaft, a cap portion, and an offset balloon. The shaft includes a proximal end, a distal end, and a central axis defined therebetween. The cap portion is coupled to the distal end of the shaft. The cap portion includes a visualization element and defines an aperture. The catheter includes an offset balloon coupled to the distal end of the shaft. The offset balloon encapsulates the cap portion and defines a center point offset relative to the central axis of the shaft.

In Example 2, the catheter of Example 1, wherein the offset balloon is mounted such that a radial distance from the central axis of the shaft to an outer surface of a first side of the offset balloon is larger than a radial distance from the central axis of the shaft to an outer surface of an opposite, second side of the offset balloon.

In Example 3, the catheter of Example 1 or Example 2, wherein the offset balloon is mounted such that a radial distance from the central axis of the shaft to the center point of the offset balloon ranges from about 0.5 millimeters to about 5 millimeters.

In Example 4, the catheter of any of Examples 1-3, wherein the offset balloon includes a neck region coupled to the distal end of the elongate shaft, the neck region defining a central axis that is offset relative to the center point of the offset balloon.

In Example 5, the catheter of any of Examples 1-4, wherein the offset balloon comprises silicone, nylon, polyamide, urethane, a polyurethane blend, a polyurethane copolymer or terpolymer, or combinations thereof.

In Example 6, the catheter of any of Examples 1-5, wherein the offset balloon, when inflated to about 21 kPa (3 psi), has an outer diameter ranging from about 1.3 centimeters (cm) (0.5 inches) to about 2.5 cm (1 inch) and a generally uniform wall thickness ranging from about 25.4 microns (0.001 inches) to about 254 microns (0.010 inches).

In Example 7, the catheter of any of Examples 1-6, wherein the offset balloon is generally spherical, conical, or ellipsoid in shape.

In Example 8, the catheter of any of Examples 1-7, wherein visualization element is a camera.

In Example 9, the catheter of Example 8, wherein the camera includes a field of view directed through the aperture of the cap portion and in a direction generally oblique or orthogonal to the central axis of the shaft.

In Example 10, a visualization catheter includes an elongate shaft including a distal end portion with a visualization means. The catheter also includes an inner balloon and an outer balloon each coupled to the distal end portion of the shaft, the inner balloon encapsulating the visualization means, the outer balloon encapsulating the inner balloon.

In Example 11, the catheter of Example 10, wherein the visualization means includes a camera or an ultrasound sensor.

In Example 12, the catheter of Example 10 or Example 11, wherein the inner balloon is adapted to inflate to a first predetermined pressure and the outer balloon is adapted to inflate to a second predetermined pressure.

In Example 13, the catheter of any one of Examples 10-12, wherein the outer balloon includes a perforated wall including a plurality of apertures therethrough.

In Example 14, the catheter of any one of Examples 10-13, wherein the inner balloon has a non-perforated wall.

In Example 15, the catheter of any one of Examples 10-14, wherein the inner and outer balloons, when inflated, have a volume ratio of the inner balloon relative to the outer balloon that ranges from about 1:2 to about 2:3.

In Example 16, the catheter of any one of Examples 10-15, wherein the inner and outer balloons each define a center point offset from a central axis defined by the shaft.

In Example 17, the method of treating a heart valve, the method including introducing a visualization catheter into a heart. The catheter can include an elongate shaft, a cap portion, and an offset balloon. The elongate shaft can include a proximal end, a distal end, and defines a central axis therebetween. The cap portion can be coupled to the distal end of the shaft. The cap portion can include a visualization element and defines an aperture. The offset balloon can be coupled to the distal end of the shaft and encapsulates the cap portion. The offset balloon can define a center point offset relative to the central axis of the shaft. The method also includes inflating the offset balloon to a predetermined pressure; and contacting a visualizing surface region of the offset balloon with an anatomical target area of the heart, the visualizing surface region of the offset balloon being located generally radial to the aperture of the cap portion.

In Example 18, the method of Example 17, wherein the center point of the offset balloon is positioned between the anatomical target area and the visualization element.

In Example 19, the method of Example 17, wherein the visualization catheter is inflated to a pressure ranging from about 14 kPa (2 psi) to about 34 kPa (5 psi).

In Example 20, the method of Example 17, wherein the visualization catheter is inflated or deflated to change a focal point of the visualization element.

The embodiments described herein may provide one or more of the following advantages. First, in some cases, the balloon-based visualization device may be configured to provide radially-directed visualization of an anatomy within a blood field to improve the consistency and quality of the visual images. More specifically, some embodiments of the device includes a shaft and a visualization element at a distal tip coupled to a distal end of the shaft, or within a distal end of the shaft, that is radially-directed relative to a central axis of the shaft configured to maintain a consistent focal length for the visualization element, such as a camera (e.g., a digital camera). For an axially-directed visualization device, the amount of force translated along the shaft of the device from a physician can directly affect the focal length of the visualization element because, when force is exerted upon a distal end of the balloon, the balloon can deform, and, ultimately, change the focal length. Unlike the axially-directed visualization device, a distal end of the radially-directed, balloon-based visualization devices provided herein can be advanced and pushed against an anatomical surface without changing, or minimally impacting, the focal distance of the visualization element because the focal distance is dependent on a radial length of the balloon, rather than a longitudinal length of the balloon.

Second, certain embodiments of the visualization device can be configured to provide visualization of anatomical areas that are radially located to the distal end of the device, e.g., anatomical areas generally parallel to the central axis defined by the distal shaft of the visualization device. For example, in some cases, the visualization device provided herein may provide visualization of blood vessel walls while the distal tip of the device is being advanced through the vessel since the visualization elements are radially-directed and face the vessel wall, rather than a lumen of the vessel wall. In contrast, when a visualization element is axially-directed, the visualization element provides visual images of anatomical areas located axially to the distal end of the device.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 5A and 5B show a plan view and a side view, respectively, of the distal portion. FIGS. 5C and 5D provide cross-sectional views along section A-A and section B-B, respectively, of the distal portion of FIG. 5A.

Figure 1A:
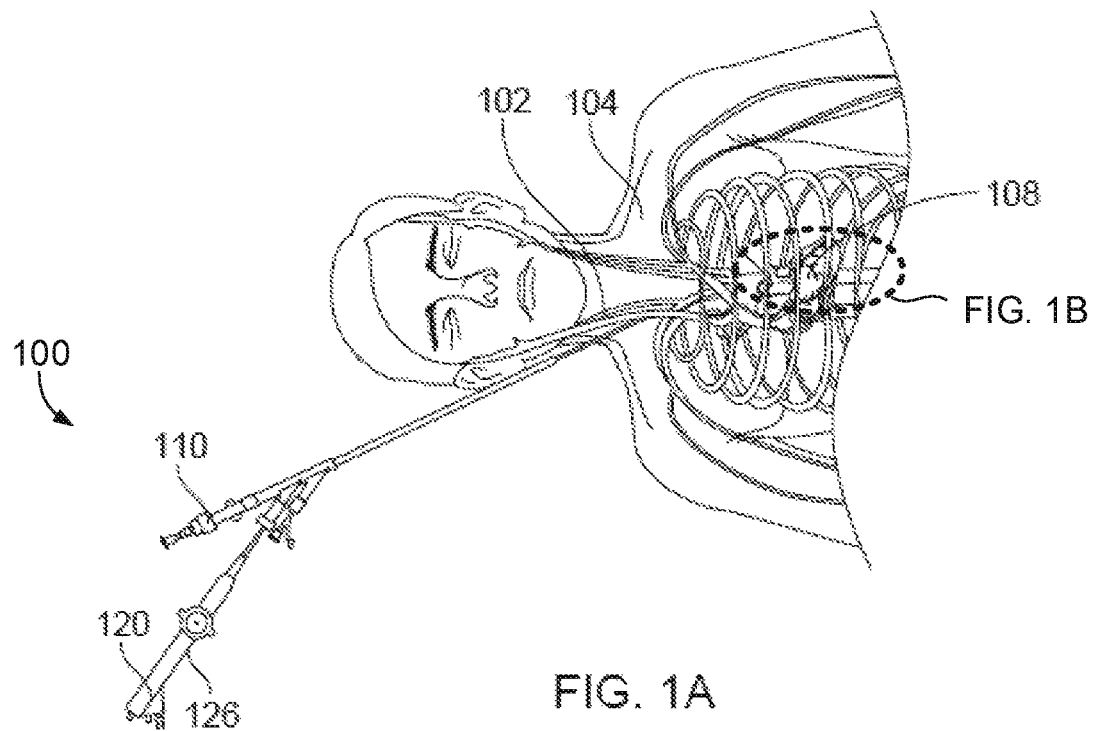
FIGS. 1A and 1B are illustrations of an embodiment of a visualization system provided herein placed within a human heart.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1B:
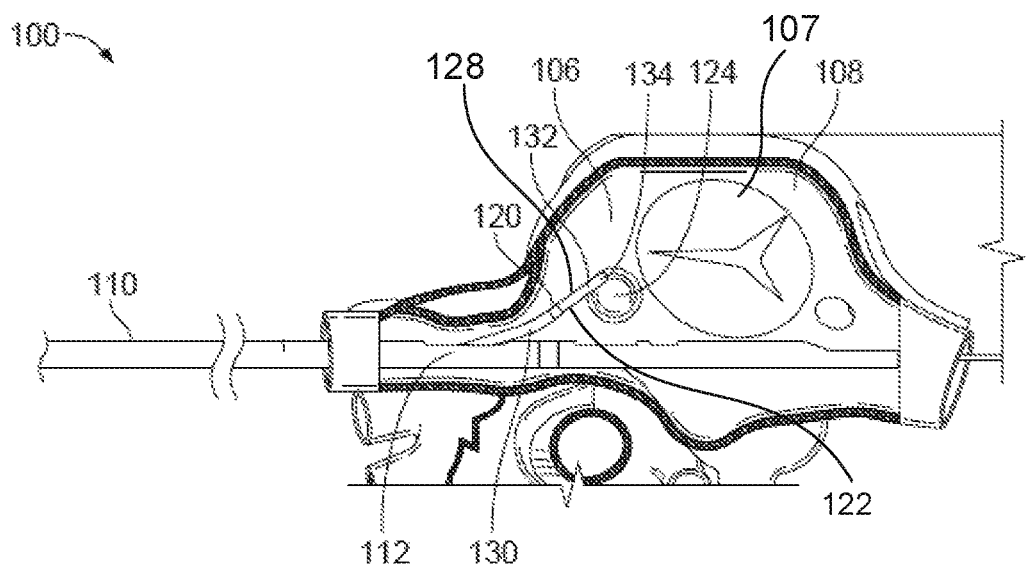

Referring to FIGS. 1A and 1B, some embodiments of a visualization system 100 provided herein can be used to repair a heart valve, such as a tricuspid valve 107. The visualization system 100 in the depicted embodiment includes multiple devices, including an introducer assembly 110 and a balloon-based visualization (BV) assembly 120. The visualization system 100 depicted in FIG. 1 is configured as a minimally invasive catheter device system in which the introducer assembly 110 can be inserted into a jugular vein 102 of the patient 104 using an over-the-wire procedure and advanced to the right atrium 106 of the heart 108. In this particular embodiment, the BV assembly 120 is configured to be inserted into the introducer assembly 110 and advanced to the heart 108 through the introducer assembly 110. More specifically, the BV assembly 120 of FIGS. 1A and 1B can be advanced into the superior vena cava and into the right atrium 106 of the heart 108 through the introducer assembly 110. In this particular embodiment depicted in FIG. 1, the BV assembly 120 includes a deflectable tip 122 that can be advanced through a distal opening 112 in the introducer assembly 110. The deflectable tip 122 can include an inflatable offset balloon 124 configured for visualizing internal anatomical features of the heart 108, as desired. The depicted balloon 124, when inflated, can help stabilize the tip 122 of the BV assembly 120 within the right atrium 106 when advanced and pressed against the walls of the atrium 106, or other interior structures such as the heart valve (e.g., tricuspid valve 107). In some cases, the visualization system 100 can be configured to mate with a secondary assembly (not shown), such as a needle assembly, which can be used in conjunction with the visualization system for suturing heart valves.

Some embodiments of the visualization system 100 and devices 110, 120 provided herein may be configured for use in minimally invasive, interventional cardiology procedures for treating cardiovascular disease. Examples of minimally invasive, interventional cardiology procedures can include, but are not limited to, percutaneous heart valve repair (e.g., tricuspid 107 or mitral valve repair) or replacement, angioplasty, stenting, atherectomy, and embolic protection related procedures. In some cases, the visualization system 100 and devices (e.g., the BV assembly 120) can be configured for repairing a heart valve, e.g., a tricuspid valve 107 or a mitral valve. According to other embodiments, the visualization system 100 and the devices can be configured for visualization within other regions of a patient's body, for example, the peripheral regions of the body. Thus, the visualization system 100 and the devices can be used for a wide range of medical applications that require visualization within a blood-field anatomy.

Still referring to FIGS. 1A and 1B, the BV assembly 120 includes a proximal portion 126, a distal portion 128, and an elongate shaft 130 therebetween. The proximal portion 126 includes a handle configured for gripping and at least one outlet connector for supplying an inflation liquid (e.g., saline solution) to the BV assembly 120. The elongate shaft 130 includes a proximal end coupled to and extending distally from the handle. The distal end 132 of the elongate shaft can be coupled to the offset balloon 124 such that at least a portion of the distal end 132 is encapsulated by the offset balloon 124. The elongate shaft 130 can include one lumen 135, or multiple lumens, for example, a first lumen for delivering an inflation medium and second lumen for receiving electric connection wires for a visualization element. As will be discussed in greater detail with FIG. 2, the distal portion 128 of the BV assembly 120 can be configured to allow a clinician to manipulate the tip 132 to directly visualize various locations within a patient's anatomy, for example, in the right atrium 106 of the heart 108 in a consistent and effective manner.

Figure 2:
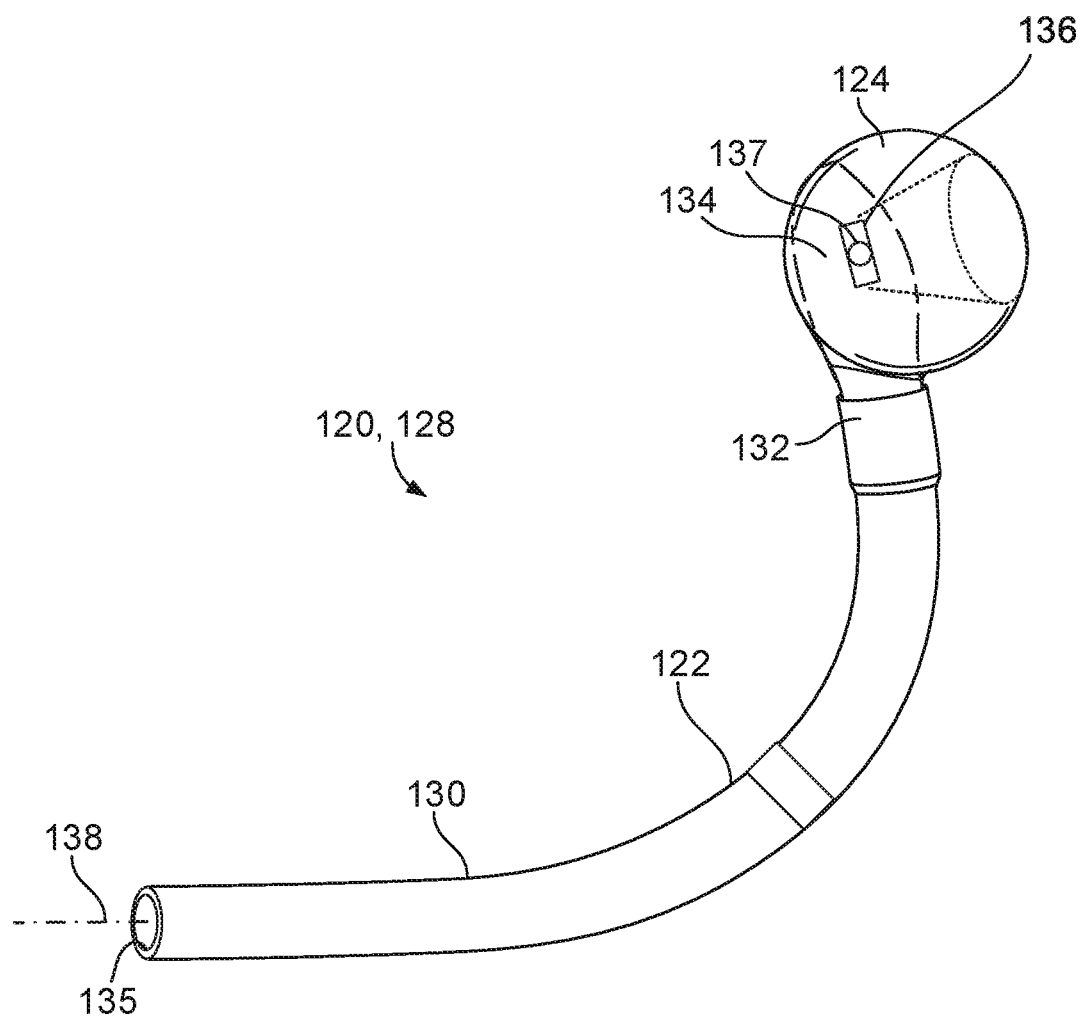
FIG. 2 is a magnified perspective view of a distal portion of a visualization device of the system of FIGS. 1A and 1B.

Referring to FIG. 2, the distal portion 128 of the BV assembly 120 includes the deflectable shaft 122, the offset balloon 124 disposed at the distal end 132 of the elongate shaft 130, and a distal cap 134 that extends distally from the distal end 132 of the shaft 130. As shown, the distal cap 134 is encapsulated within the offset balloon 124. The deflectable shaft 130 defines a lumen and a central axis 138 extending from the proximal end to the distal end 132. In some cases, the shaft 130 of the BV assembly 120 can be configured to deflect (i.e., bend) at a predetermined angle and curvature when in a non-restrained state. In some cases, the deflectable tip 122 may be adjustable to various angles and curvatures, as desired. The shaft 130 can be made of various polymeric materials. Suitable shaft materials can include, but are not limited to, polyurethanes, polyethylene terephthalate (PET), poly(ethylene oxide) (PEO), and poly (butylene terephthalate) copolymers (PBT), polyamides, and combinations thereof. The shaft 130 can be can be made using processes that include, but are not limited to, extrusion, braiding, injection molding, and combinations thereof.

In various cases, the BV assembly 120 can include an offset balloon 124. In various cases, as will be discussed in greater detail with reference to FIGS. 3A and 3B, the offset balloon 124 can be configured to couple to the shaft 130 such that the balloon 124 is positioned offset from the central axis 138 of the shaft.

The distal cap 134 can be disposed within the offset balloon 124 such that at least a portion of the inner surface of the balloon 124 contacts the distal cap 134, in some cases. The distal cap 134 can define at least one aperture 136, configured to allow a visualization element 137, such as a camera (e.g., a CCD/CMOS digital imaging camera) or an ultrasound sensor (e.g., a three-dimensional digital ultrasound sensor), to receive visual images through the offset balloon and provide the visual images to a practitioner during a medical procedure. In some cases, the distal cap 134 can include multiple apertures 136. In some cases, the distal cap 134 can include multiple visualization elements 137. The cap portion 134, as depicted in FIG. 2, includes a camera directed in a direction oblique and/or orthogonal to the central axis 138 of the shaft 130 (as depicted by dotted lines in the FIG. 2) to facilitate radial-directed viewing of an internal anatomy, such as the interior heart wall.

Figure 3A:
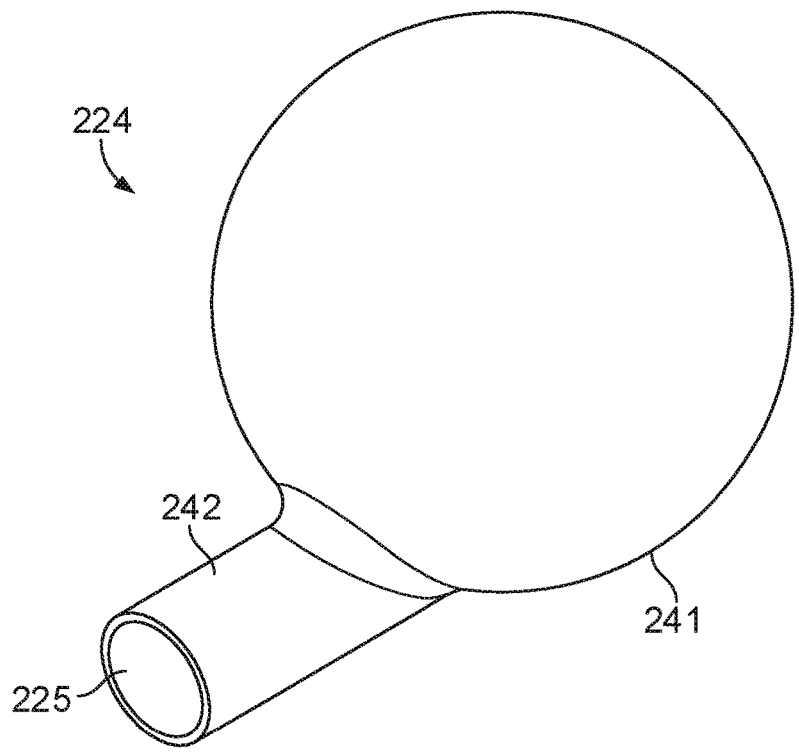
FIGS. 3A and 3B are a perspective view and a side view of an exemplary balloon, in accordance with some embodiments provided herein.
Figure 3B:
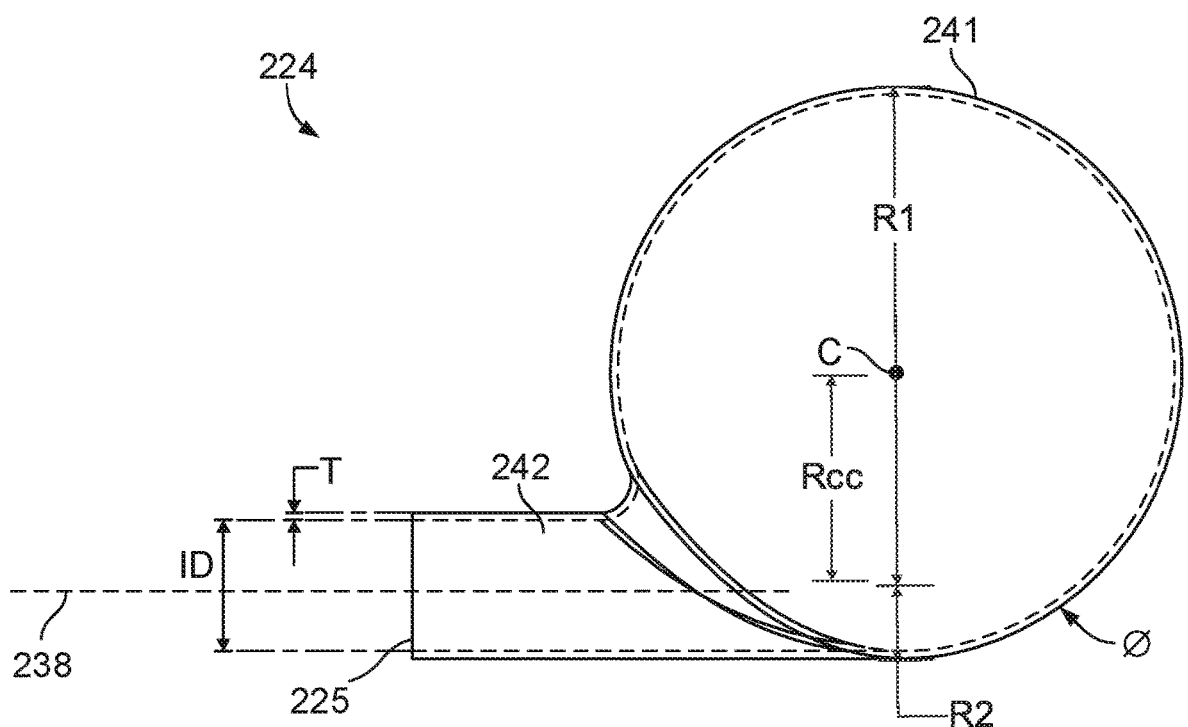

Referring to FIGS. 3A and 3B, some embodiments of the offset balloon 224 include a generally symmetrical body 241 and a neck region 242 extending from the body 241. The neck region 242 of the offset balloon 224 defines an inner diameter and an opening 225 configured for receiving, or, alternatively, being received by the shaft (e.g., shaft 130 of FIG. 1) of the BV assembly. The neck region 242, when coupled to a distal end of the elongate shaft (e.g., the distal end 132 of shaft 130 of FIG. 1), offsets the balloon 224 with respect to the central axis 238 of the shaft to facilitate radially-directed viewing by the visualization element 237 disposed within the distal cap of the BV assembly. In particular, the offset balloon 224 can be mounted to a distal end of the shaft such that the central axis 238 of the shaft does not pass through a center point "C" of the offset balloon, as shown in FIG. 3B. As such, the center point C of the offset balloon 224 may be offset from the central axis 238 of the shaft of the BV assembly by a predetermined central-axis-to-center-point radial distance "Rcc". In some cases, the predetermined central-axis-to-center-point radial distance Rcc can range from about 0.001 inches to about 0.394 inches (0.25 millimeters (mm) to about 10 mm). For example, in some cases, the predetermined central-axis-to-center-point radial distance Rcc can range from about 0.01 inches to about 0.02 inches (about 0.25 mm to about 0.5 mm), from about 0.02 inches to about 0.04 inches (from about 0.5 mm to about 1 mm), from about 0.04 inches to about 0.12 inches (from about 1 mm to about 3 mm), from about 0.12 inches to about 0.20 inches (from about 3 mm to about 5 mm), or from about 0.02 inches to about 0.2 inches (from about 0.5 mm to about 5 mm). The offset balloon 224 may include a first radial distance R1 from the central axis of the shaft to the outer surface of the balloon along a first side is larger than a second radial distance R2 from the central axis of the shaft to the outer surface of the balloon on an opposite, second side. In some cases, the ratio of the first and second radial distances can range from 2:1 to about 20:1 (e.g., from about 2:1 to about 3:1, from about 3:1 to about 4:1, from about 4:1 to about 5:1, from about 5:1 to about 6:1, from about 6:1 to about 7:1, from about 7:1 to about 8:1, from about 8:1 to about 9:1, from about 9:1 to about 10:1, from about 10:1 to about 15:1, and from about 15:1 to about 20:1), including all ranges and values.

The BV assembly provided herein can include a wide variety of different balloon shapes. For example, in some cases, the offset balloon, when inflated, can have a generally spherical, conical, or ellipsoid shape. In some cases, the cross-sectional shape of the inflated offset balloon can include, but is not limited to, a generally frustoconical, cone, polygonal, or oval shape.

The BV devices provided herein can include an offset balloon 224 that is scalable to a range of sizes. In some cases, the offset balloon 224, when inflated, can have an average dimension (e.g., a diameter of a spherical balloon) or a maximum dimension (e.g., a major diameter of an oval balloon) ranging from about 1.3 centimeters (cm) (0.5 inches) to about 2.5 cm (1 inch). For example, in some cases, the offset balloon 224, when inflated (e.g., inflated to about 21 kPa (3 psi)), can have an outer diameter ranging from about 1.3 centimeters (cm) (0.5 inches) to about 2.5 cm (1 inch) and a generally uniform wall thickness ranging from about 0.001 inches to about 0.010 inches.

The offset balloon 224 of the BV assembly provided herein can be made of one or more transparent or translucent polymeric materials. In some cases, the offset balloon 224 is made of an elastic material adapted to allow the balloon to conform to an anatomical surface, such as an atrial or ventricle wall, or a leaflet. In some cases, the offset balloon 224 can be made of a material that can be processed using various manufacturing methods, such as injection molding, blow molding, extrusion, and the like. Components of the BV assembly provided herein can be assembled together using manufacturing processes such as adhesive bonding, heat bonding (e.g., laser bonding), over-molding, press fitting, and combinations thereof.

Suitable materials for the offset balloon 224 can include, but are not limited to, silicone, nylon, polyamide, urethane, a polyurethane blends, polyurethane copolymers (e.g., polyisobutylene polyurethane copolymers), and combinations thereof. In some cases, suitable materials, such as silicone, can provide several advantages as a balloon material. In some cases, suitable materials provided herein may include materials having properties that allow the balloon to be optical transparent within a blood environment, highly elastic, and re-sealable in certain circumstances. For example, silicone may be used as an exemplary self-sealing material when penetrated by another component or assembly of the visualization system, such as a needle, in some cases.

The offset balloon 224 of the BV assembly or device can be a weeping balloon. A weeping balloon is a balloon defining a plurality of perforations such that an inflation media used for inflating the balloon can flow from an inner cavity of the balloon to an exterior surface of the balloon. When the inflation media flow out of the balloon onto the exterior surface of the balloon, the inflation media can clear blood from the exterior surface of the balloon to facilitate visualization of an anatomical surface that is in contact with the balloon.

Figures 4A, 4B, 4C:
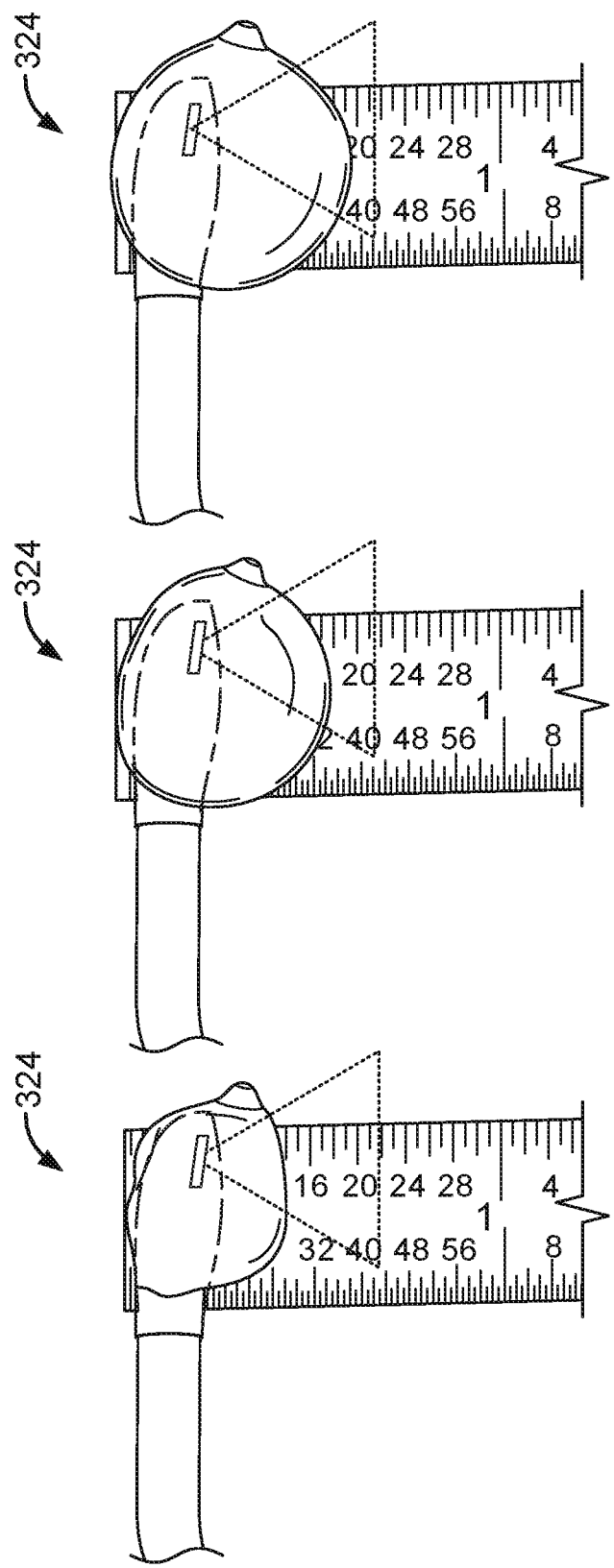
FIGS. 4A-4C are perspective views of an exemplary balloon in various inflated states in which the balloon is inflated to different pressures.

Referring to FIGS. 4A-4C, an exemplary offset balloon 324 is shown inflated to various pressures. In some cases, the offset balloon 324 can be inflated to a low, a moderate and a high pressure to distend (i.e., increases in size) the offset balloon 324 to varying degrees. In FIG. 4A, the offset balloon 324 was inflated to a low pressure (e.g., about 3.4 Kpa to about 6.9 KPa, or about 0.5 psi to about 1 psi), creating a field of view (depicted by the triangles shown in the figures) for a visualization device within the offset balloon that has a length of about 6.35 mm (0.25 inches). In FIG. 4B, the offset balloon 324 was inflated to a moderate pressure, e.g., from about 7 kilopascals (kPa) to about 14 kPa (from about 1 psi to about 2 psi), creating a field of view of ranging from about 7.6 mm to about 10.1 mm (0.3 to about 0.4 inches). In FIG. 4C, the offset balloon 324 was inflated to a high pressure, ranging from about 14 kPa to about 21 kpa (2 psi to about 21 kPa or 3 psi), resulting in a field of view of about 1.27 cm (0.5 inches). Accordingly, as shown, some embodiments of the visualization device provided herein include an offset balloon configured to distend (increase in size) to varying degrees depending on the pressure.

In some embodiments, the BV assembly or device provided herein can include a offset balloon 324 that can distend such that a field of view from 10%, 20%, 30%, 40%, 50%, 60%, 70%, 80%, 90%, 100%, or greater than 100% in size relative to the field of view of the balloon 324 when in a non-inflated state. In some embodiments, the field of view of an offset balloon 324 can range from about 2.5 mm (0.1 inches) to about 25 mm (1 inch), including all values and ranges thereof. For example, the offset balloon 324 of the BV assembly or device provided herein can, when pressurized from a range of about 7 kPa to about 82 kPa (about 1 psi to about 12 psi), provide a field of view ranging from about 2.5 mm (0.1 inches) to about 5.1 mm (0.2 inches), about 5.1 mm (0.2 inches) to about 7.6 mm (0.3 inches), from about 7.6 mm (0.3 inches) to about 10 mm (0.4 inches), from about 10 mm (0.4 inches) to about 12.7 mm (0.5 inches), from about 12.7 mm (0.5 inches) to about 15 mm (0.6 inches), from about 15 mm (0.6 inches) to about 18 mm (0.7 inches), from about 18 mm (0.7 inches) to about 20 mm (0.8 inches), from about 20 mm (0.8 inches) to about 23 mm (0.9 inches), from about 23 mm (0.9 inches) to about 25 mm (1 inch), from about 2.5 mm (0.1 inches) to about 7.6 mm (0.3 inches), from about 2.5 mm (0.1 inches) to about 10 mm (0.4 inches), from about 2.5 mm (0.1 inches) to about 12.7 mm (0.5 inches), from about 2.5 mm (0.1 inches) to about 15 mm (0.6 inches), from about 2.5 mm (0.1 inches) to about 18 mm (0.7 inches), from about 2.5 mm (0.1 inches) to about 20 mm (0.8 inches), from about 2.5 mm (0.1 inches) to about 23 mm (0.9 inches), from about 5.1 mm (0.2 inches) to about 10 mm (0.4 inches), from about 5.1 mm (0.2 inches) to about 12.7 mm (0.5 inches), or from about 5.1 mm (0.2 inches) to about 15 mm (0.6 inches).

Figure 5A:
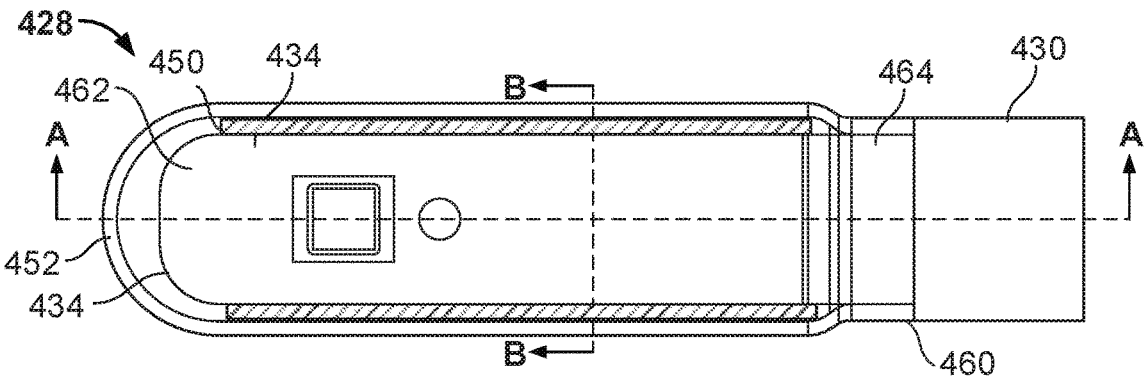
FIGS. 5A-5D provide various views of a distal portion of another exemplary visualization device that includes a dual-balloon design.
Figure 5B:
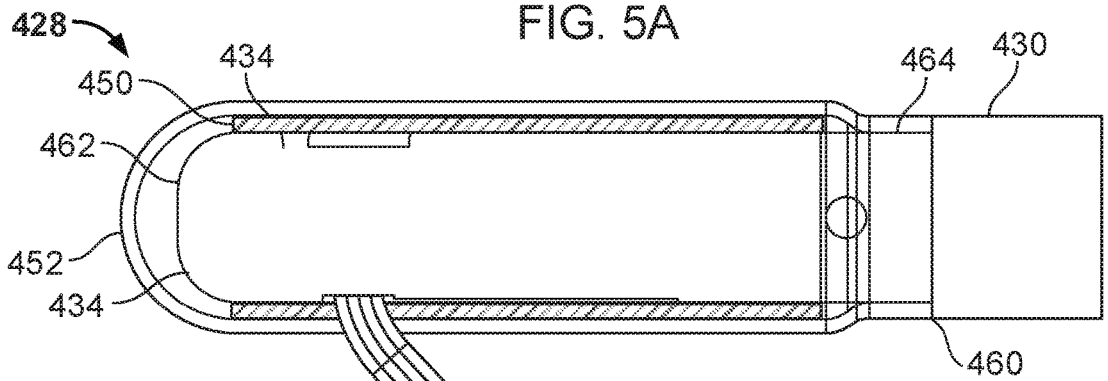
Figure 5C:
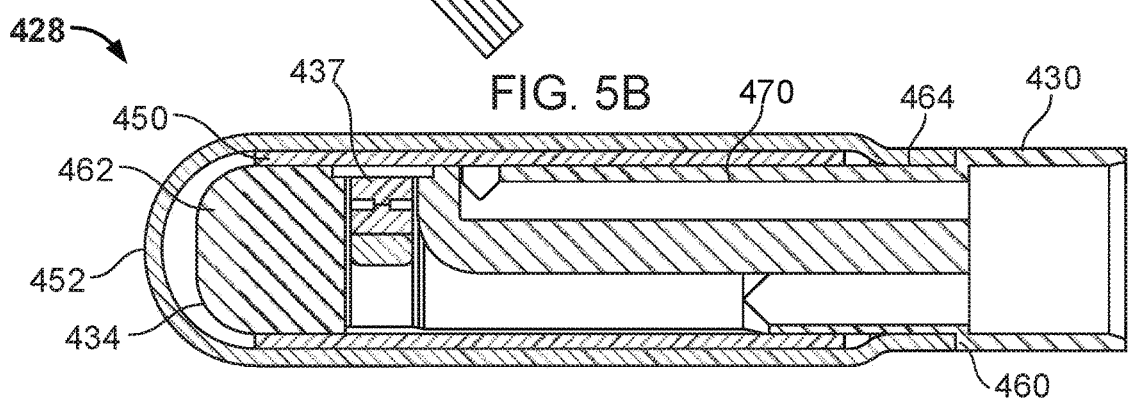
Figure 5D:
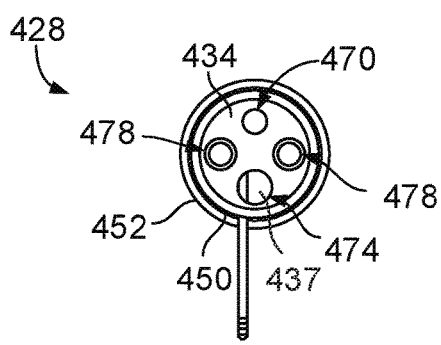

FIGS. 5A-5D provide various views of a distal portion 428 of another exemplary visualization device, in accordance with some embodiments provided herein. FIGS. 5A and 5B show a plan view and a side view, respectively, of the distal portion 428. FIGS. 5C and 5D provide cross-sectional views along A-A and B-B of the distal portion 428 of FIG. 5A. As shown, the distal portion 428 of the depicted visualization device is a dual balloon-based visualization device that includes an elongate shaft 430 including a distal end portion with a visualization means, a first balloon (e.g., an inner balloon 450), a second balloon (e.g., an outer balloon 452) and a distal cap 434 having a proximal end 460 and a distal end 462. In the depicted embodiment of the exemplary device, the inner balloon 450 is coupled to the distal cap 434 at a proximal neck portion 464 located at a proximal end 460 of the distal cap 434. The inner balloon 450, as shown in FIGS. 5A-5D, encapsulates the distal end 462 of the cap 434. The depicted embodiment of the exemplary device also shows that the outer balloon 452 is coupled to the distal cap 434 at the proximal neck portion 464 and encapsulates the inner balloon 450 and the distal end 462 of the distal cap 434. In some embodiments, the BV devices provided herein can include two or more balloons configured for improving visualization during a medical procedure. In some cases, the visualization device can include three, four, five, or more than five balloons.

In the depicted embodiment of the visualization device, the distal cap (also including elongate shaft) can include multiple components therein and define multiple lumens for receiving the components. The distal cap can optionally include a lumen 470 for receiving a visualization element 437 (e.g., a radiation-emitting element) configured for providing illumination at the distal end of the device. The distal cap can, in some cases, include one or more lumens 474 for receiving a visualization element 437 provided herein and wiring therefor. Some embodiments of the device can include a distal cap with one or more lumens 478 for receiving an inflation liquid (e.g., saline solution). In some cases, the lumens within the distal cap and shaft have an inner diameter ranging from about 0.5 mm (0.0200 inches) to about 3.8 mm (0.15 inches). The distal cap have an outer diameter ranging from about 1.3 mm (0.050 inches) to about 11.4 mm (0.45 inches), including all ranges and values therebetween.

In some cases, the outer balloon 452 is a weeping balloon that includes a plurality of perforations. In some cases, the inner balloon 450 is not a weeping balloon, i.e., the inner balloon 450 has non-perforated walls.

Figure 6A:
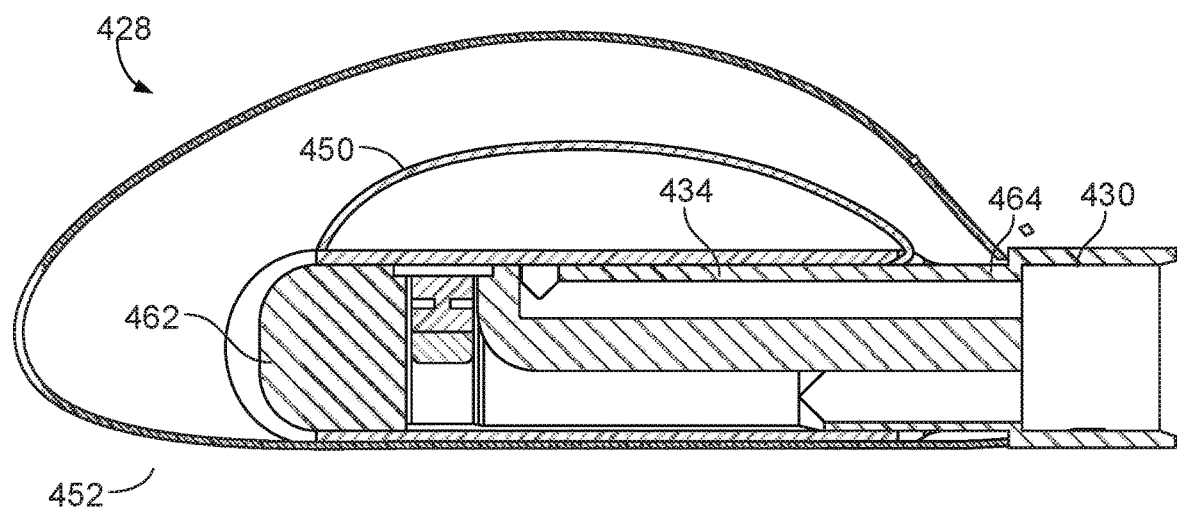
FIGS. 6A and 6B show the device of FIGS. 5A-5D in partially and fully inflated states, respectively.
Figure 6B:
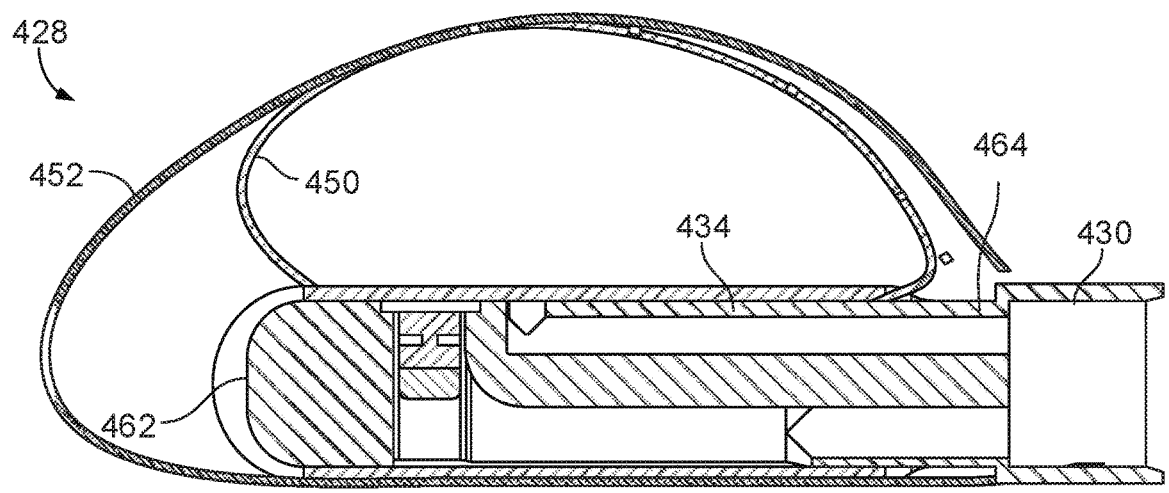

Referring to FIGS. 6A and 6B, in various cases, the distal portion 428 of the BV devices provided herein include a first offset balloon (e.g., inner balloon 450) and a second offset balloon (e.g., outer balloon 452) that are sized differently. FIG. 6A shows the inner and outer balloons 450, 452 both at a partially inflated state and FIG. 6B shows the inner and outer balloons 450, 452 both at a fully inflated state. The inner and outer balloons 450, 452, in some cases, are coupled to separate pressure lines and therefore can be inflated independently. In some cases, the inner and outer balloons 450, 452, when partially or fully inflated, are sized such that the ratio of the inner balloon volume relative to the outer balloon volume can range from about 1:2 to about 1:50 (e.g., from about 1:2 to about 1:3, from about 1:3 to about 1:4, from about 1:4 to about 1:5, from 1:5 to about 1:6, from about 1:6 to about 1:7, from about 1:7 to about 1:8, from about 1:8 to about 1:9, from about 1:9 to about 1:10, from about 1:10 to about 1:15, and from about 1:15 to about 1:20).

In some cases, the inner and outer balloons 450, 452 can be configured to allow a practitioner to inflate the inner balloon 450 to a higher pressure than the outer balloon 452. For example, the inner balloon 450 can be adapted to be inflated to a first predetermined pressure and the outer balloon 452 can be adapted to be inflated to a second predetermined pressure. In some cases, the first predetermined pressure can range from about 0.7 kPa to about 138 kPa (about 0.1 psi to about 20 psi), including all values and ranges therebetween. In some cases, the second predetermined pressure can range from about 0.7 kPa to about 34 kPa (about 0.1 psi to about 5 psi), including all values and ranges therebetween. The first predetermined pressure can, in some cases, be about 5%, about 10%, about 20%, about 30%, about 40%, about 50%, about 60%, about 75%, or about 100% greater than the second predetermined pressure. In some cases, the inner balloon provides the benefit of providing a consistent focal length for the visualization element and the outer balloon 452 provided the benefit of clearing blood (via weeping) from the outer surface of the distal end portion of the device. The outer balloon 452 can also provide the benefit of absorbing shock from internal movements such as a pulsating heart wall.

The first and second balloons (e.g., the inner and outer balloons 450, 452) of the device provided herein can be made of the same or different materials. In some cases, the first and second balloons can be made of materials having different mechanical properties. For example, in some cases, the first balloon can be made of a low durometer silicone and the second balloon can be made of a high durometer silicone. In some cases, the first balloon can be made of a material having a lower elasticity or Young's modulus than second balloon.

It should be understood that one or more design features of the devices provided herein can be combined with other features of other devices provided herein. In effect, hybrid designs that combine various features from two or more of the device designs provided herein can be created, and are within the scope of this disclosure.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein. All references, publications, and patents referred to herein, including the figures and drawings included therewith, are incorporated by reference in their entirety.

We claim:

1. A visualization catheter comprising:
    an elongate shaft including a proximal end, a distal end, and a central axis defined therebetween;
    a cap element attached to and extending distally from the distal end of the shaft, the cap element defining an aperture and having a visualization element disposed within the aperture; and
    wherein an offset balloon is coupled to the distal end of the shaft, and wherein the offset balloon completely encapsulates the cap element and the distal end of the shaft such that the offset balloon defines a distal terminal end of the visualization catheter, wherein the offset balloon defines a center point offset relative to the central axis of the shaft;
    wherein the offset balloon includes a body region and a cylindrical neck region coupled to the distal end of the elongate shaft, wherein the cylindrical neck region is coaxial with the central axis of the shaft and the body region defines a center point that is offset relative to the central axis of the shaft, wherein the body region extends from the cylindrical neck region with an outer extent of a first side of the body region aligned with an outer extent of the cylindrical neck region, and an outer extent of a second opposite side of the body region extending radially outward from the cylindrical neck region.

2. The catheter of claim 1, wherein the offset balloon is mounted such that a radial distance from the central axis of the shaft to the center point of the offset balloon ranges from 0.5 millimeters to 5 millimeters.

3. The catheter of claim 1, wherein a portion of an inner surface of the body region of the offset balloon contacts a portion of the cap.

4. The catheter of claim 1, wherein the offset balloon comprises silicone, nylon, polyamide, urethane, a polyurethane blend, a polyurethane copolymer or terpolymer, or combinations thereof.

5. The catheter of claim 1, wherein the body region of the offset balloon, when inflated to 21 kPa (3 psi), has an outer diameter ranging from 1.3 centimeters (cm) (0.5 inches) to 2.5 cm (1 inch) and a uniform wall thickness ranging from 25.4 microns (0.001 inches) to 254 microns (0.010 inches).

6. The catheter of claim 1, wherein the offset balloon is spherical, conical, or ellipsoid in shape.

7. The catheter of claim 1, wherein visualization element is a camera.

8. The catheter of claim 7, wherein the camera includes a field of view directed through the aperture of the cap element and in a direction oblique or orthogonal to the central axis of the shaft.

9. A method of treating a heart valve, the method comprising:
   introducing a visualization catheter into a heart, the catheter comprising:
      an elongate shaft including a proximal end, a distal end, and defining a central axis therebetween;
      a cap element attached to and extending distally from the distal end of the shaft, the cap element defining an aperture and having a visualization element disposed within the aperture; and
      an offset balloon coupled to the distal end of the shaft and completely encapsulating the cap element and the distal end of the shaft such that the offset balloon defines a distal terminal end of the visualization catheter, the offset balloon defining a center point offset relative to the central axis of the shaft;
   wherein the offset balloon includes a body region and a cylindrical neck region coupled to the distal end of the elongate shaft, wherein the cylindrical neck region is coaxial with the central axis of the shaft and the body region defines a center point that is offset relative to the central axis of the shaft, wherein the body region extends from the cylindrical neck region with an outer extent of a first side of the body region aligned with an outer extent of the cylindrical neck region, and an outer extent of a second opposite side of the body region extending radially outward from the cylindrical neck region;
   inflating the body region of the offset balloon to a predetermined pressure; and
   contacting a visualizing surface region of the offset balloon with an anatomical target area of the heart, the visualizing surface region of the offset balloon being located radial to the aperture of the cap element.

10. The method of claim 9, wherein the center point of the offset balloon is positioned between the anatomical target area and the visualization element.

11. The method of claim 9, wherein the visualization catheter is inflated to a pressure ranging from 14 kPa (2 psi) to 34 kPa (5 psi).

12. The method of claim 9, wherein the visualization catheter is inflated or deflated to change a focal point of the visualization element.

* * * * *